US011642137B2

(12) United States Patent
Mulqueen et al.

(10) Patent No.: US 11,642,137 B2
(45) Date of Patent: May 9, 2023

(54) ADJUSTABLE FEMORAL NECK OSTEOTOMY GUIDE

(71) Applicant: Zimmer Biomet Pty Ltd, Belrose (AU)

(72) Inventors: Marika Mulqueen, Strathdale (AU); Massoud Akbarshahi, Belrose (AU); Mark Mottram, Penshurst (AU)

(73) Assignee: Zimmer Biomet Pty Ltd, Belrose (AU)

( * ) Notice: Subject to any disclaimer, the term of this patent is extended or adjusted under 35 U.S.C. 154(b) by 154 days.

(21) Appl. No.: 17/079,019

(22) Filed: Oct. 23, 2020

(65) Prior Publication Data
US 2021/0121184 A1   Apr. 29, 2021

Related U.S. Application Data

(60) Provisional application No. 62/926,893, filed on Oct. 28, 2019.

(51) Int. Cl.
*A61B 17/15* (2006.01)
*A61B 34/10* (2016.01)
*A61B 17/16* (2006.01)

(52) U.S. Cl.
CPC ........ *A61B 17/151* (2013.01); *A61B 17/1668* (2013.01); *A61B 34/10* (2016.02); *A61B 2034/104* (2016.02); *A61B 2034/105* (2016.02); *A61B 2034/107* (2016.02)

(58) Field of Classification Search
CPC ... A61B 17/15; A61B 17/1668; A61B 17/175; A61B 2090/061; A61B 2090/067; A61B 90/11
See application file for complete search history.

(56) References Cited

U.S. PATENT DOCUMENTS

| | | | |
|---|---|---|---|
| 4,959,066 A | * | 9/1990 | Dunn ............... A61B 17/15 606/89 |
| 6,258,097 B1 | | 7/2001 | Cook et al. |
| 8,070,752 B2 | | 12/2011 | Metzger et al. |
| 8,092,465 B2 | | 1/2012 | Metzger et al. |
| 8,282,646 B2 | | 10/2012 | Schoenfeld et al. |
| 8,298,237 B2 | | 10/2012 | Schoenfeld et al. |
| 8,407,067 B2 | | 3/2013 | Uthgenannt et al. |

(Continued)

FOREIGN PATENT DOCUMENTS

| | | |
|---|---|---|
| EP | 1588668 B1 | 12/2008 |
| EP | 3815630 A1 | 5/2021 |

(Continued)

OTHER PUBLICATIONS

"Australian Application Serial No. 2020257132, First Examination Report dated Jun. 29, 2021", 4 pgs.

(Continued)

*Primary Examiner* — Samuel S Hanna
(74) *Attorney, Agent, or Firm* — Schwegman Lundberg & Woessner, P.A.

(57) ABSTRACT

An orthopedic assembly is disclosed. This orthopedic assembly can include a ring portion, a second portion and indicia. The ring portion can define an aperture configured to allow the ring portion to seat on a head of a bone. The second portion can extend from the ring portion. The second portion can define a slot that is curved along a first length. The indicia can extend along a portion of one or both of the ring portion and the second portion.

15 Claims, 16 Drawing Sheets

(56) References Cited

U.S. PATENT DOCUMENTS

| | | |
|---|---|---|
| 8,473,305 B2 | 6/2013 | Belcher et al. |
| 8,568,487 B2 | 10/2013 | Witt et al. |
| 9,241,745 B2 | 1/2016 | Smith et al. |
| 9,345,548 B2 | 5/2016 | Schoenefeld et al. |
| 9,907,659 B2 | 3/2018 | Belcher et al. |
| 9,931,168 B2 | 4/2018 | Brown |
| 2004/0236341 A1 | 11/2004 | Petersen |
| 2008/0257363 A1 | 10/2008 | Schoenefeld et al. |
| 2014/0276866 A1 | 9/2014 | Endsley et al. |
| 2016/0374697 A1* | 12/2016 | Kehres .................. A61B 17/15 606/87 |
| 2021/0236145 A1* | 8/2021 | Beverland ............... A61B 17/15 |
| 2021/0259705 A1* | 8/2021 | Beverland ............... A61B 90/06 |
| 2022/0287722 A1 | 9/2022 | Mulqueen et al. |

FOREIGN PATENT DOCUMENTS

| | | |
|---|---|---|
| WO | WO-2010129870 A1 | 11/2010 |
| WO | WO-2020001830 A1 | 1/2020 |
| WO | WO-2020002190 A1 | 1/2020 |

OTHER PUBLICATIONS

"Australian Application Serial No. 2020257132, Response filed Jan. 24, 2022 to Subsequent Examiners Report dated Nov. 25, 2021", 8 pgs.

"Australian Application Serial No. 2020257132, Response filed Aug. 20, 2021 First Examination Report dated Jun. 29, 2021", 15 pgs.

"Australian Application Serial No. 2020257132, Response filed Nov. 11, 2021 to Subsequent Examiners Report dated Sep. 16, 2021", 11 pgs.

"Australian Application Serial No. 2020257132, Subsequent Examiners Report dated Sep. 16, 2021", 6 pgs.

"Australian Application Serial No. 2020257132, Subsequent Examiners Report dated Nov. 25, 2021", 3 pgs.

"European Application Serial No. 20204413.7, Extended European Search Report dated Mar. 22, 2021", 7 pgs.

"European Application Serial No. 20204413.7, Response filed Nov. 5, 2021 to Extended European Search Report dated Mar. 22, 2021", 17 pgs.

Lustig, Sebastien, "Step by Step Guide How to template the Hip", [Viewed on internet on Nov. 22, 2021] Viewed on internet. <URL: http://orthopedie-lyon.fr/wp-content/uploads/2016/12/template-the-hip-min.pdf>, (2016), 25 pgs.

U.S. Appl. No. 17/684,828, filed Mar. 2, 2022, Surgical Instruments Including Marking Tools and Cut Guides.

\* cited by examiner

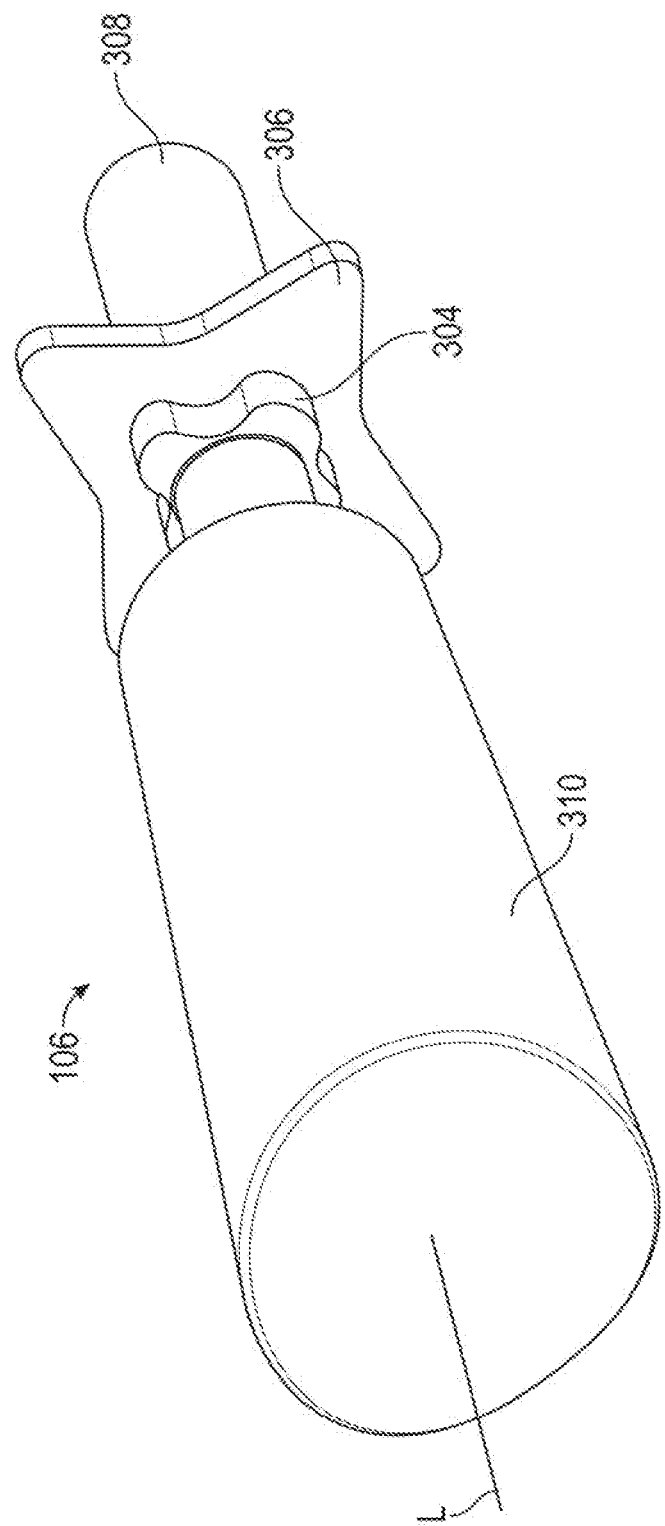

ADJUSTABLE FEMORAL NECK OSTEOTOMY GUIDE

CLAIM OF PRIORITY

This application claims the benefit of U.S. Provisional Patent Application Ser. No. 62/926,893, filed on Oct. 28, 2019, the benefit of priority of which is claimed hereby, and which is incorporated by reference herein in its entirety.

FIELD

The present subject matter relates to surgical apparatuses, systems and methods, and more particularly, to surgical apparatuses and related systems and methods that allow a cut guide to be positioned to correspond to the anatomy for an individual patient.

BACKGROUND

Resection or cut guides are used in various orthopedic surgical procedures including in a total femoral hip arthroplasty. Part of this procedure removes a damaged head of the femur with the guide aiding such removal by guiding the cut(s) (also termed resection(s)) performed by a surgeon. Prosthetic devices recreating the hip joint are then implanted on the remaining bone of the femur and in bone of the patient's hip.

OVERVIEW

This disclosure pertains generally to apparatuses, systems and methods that help overcome challenges that can arise during orthopedic surgery. One such challenge can be properly locating a cut guide taking into account a patient's anatomy (e.g., bone size, shape and orientation). This anatomy varies from patient to patient. It can be time consuming and sometime complicated for the surgeon to make appropriate anatomical measurements, adjust instruments such as the cut guide according to such measurements and locate the cut guide properly and perform other tasks related to the orthopedic surgery.

The present inventors have recognized, among other things, positioning apparatuses (also commonly called an alignment guides) that facilitate a desired positioning for a cut guide that take into account a patient's individual anatomy. Such positioning apparatuses are configured to reduce surgical time and complexity as they are intuitive to use and have reduced complexity as compared with traditional alignment and cut guides.

Although described in reference to a femur, the apparatuses, systems and methods of the present application are applicable to other bones or bone portions including the humerus and distal femur.

According to one aspect this application, the present inventors have recognized, among other things, orthopedic alignment and cut guides can benefit from virtual surgery planning systems and methods. Such systems and methods can facilitate the virtual identification of bone that should be removed and can virtually identify a shape, angle, and/or length of bone portions to be removed. The systems and methods can additionally facilitate the selection of appropriate settings for positioning a cut guide with one or more alignment guides such that the cut guide has a patient-appropriate size and/or angle of cut. Using the virtual surgery planning systems and methods, procedures such as resection of the neck of a femur below the femoral head can be simplified so as to be performed more rapidly, with a lesser number of measurements having to be performed by the surgeon, and in a more reproducible surgical manner. Thus, the present inventors have invented, apparatuses systems and methods that include an adjustable cut guide and adjusting settings on the cut guide based on anatomy of the patient. In some cases, the techniques discussed can be used in combination with output from a visualization system to modify the position of the cut guide to be specific to an individual patient's anatomy.

To further illustrate the apparatuses, systems and methods disclosed herein, the following non-limiting examples are provided:

Example 1 is an orthopedic assembly optionally comprising any one or combination of: a ring portion that can define an aperture configured to allow the ring portion to seat on a head of a bone; a second portion that extends from the ring portion, wherein the second portion can define a slot that is curved along a first length; and indicia extending along a portion of one or both of the ring portion and the second portion.

Example 2 is the orthopedic assembly of Example 1, wherein the second portion can define a first plurality of detents arranged along a first side of the slot for at least a portion of the first length and can define a second plurality of detents arranged along a second side of the slot for at least the portion of the first length, wherein the second plurality of detents can oppose and can be generally aligned with the first plurality of detents across a width of the slot.

Example 3 is the orthopedic assembly of any one or any combination of Examples 1-2, wherein the second portion can have an outer surface that is curved along an extent outward of the ring portion, and wherein the outer surface and the curved slot can provide the second portion with a uniform width between the outer surface and the slot for the first length.

Example 4 is the orthopedic assembly of Example 3, wherein the second portion can define a third plurality of detents arranged along at least a portion of the outer surface of the second portion, wherein the third plurality of detents can generally align with the first plurality of detents.

Example 5 is the orthopedic assembly of any one or any combination of Examples 1-4, optionally further comprising a guide leg defining a resection slot configured to guide removal of the head of the bone, wherein the guide leg can be configured to couple to the second portion via a first projection that is received in the slot.

Example 6 is the orthopedic assembly of Example 5, wherein the guide leg can define a plurality of pin holes therein, and wherein the first projection can be cannulated defining one pin hole of the plurality of pin holes.

Example 7 is the orthopedic assembly of any one or any combination of Examples 5-6, wherein the guide leg can have a second projection extending substantially parallel with the first projection, and wherein the second projection and the first projection can be spaced apart such that the first projection can be received in the slot and the second projection engages the outer surface of the second portion.

Example 8 is the orthopedic assembly of any one or any combination of Examples 5-7, wherein the guide leg can optionally further define a slot spaced from the resection slot, and can optionally further comprise a referencing tool configured to be received in the slot of the guide leg, and wherein the guide leg and referencing tool can be moveable relative to one another via the slot.

Example 9 is the orthopedic assembly of Example 8, wherein the referencing tool can be configured to project from the guide leg to engage a saddle on a neck of the bone distal of the head.

Example 10 is the orthopedic assembly of Example 9, wherein movement of the guide leg relative to the referencing tool via the slot can adjust a length of resection guided by the resection slot to the neck of the bone.

Example 11 is the orthopedic assembly of Example 10, wherein the referencing tool and the guide leg can each have indicia, including indicia indicative of a distance between the saddle and a center line of the neck of the bone, and wherein the referencing tool can be non-circular in cross-section at a portion that engages the saddle point thereby allowing the referencing tool to be rotated to adjust the guide leg position relative to the neck of the bone.

Example 12 is the orthopedic assembly of any one or any combination of Examples 1-11, wherein the ring portion and the second portion can have a first side and a second side, and wherein the first side can have a substantially similar shape as the second side such that the orthopedic assembly can be reversable and can be configured for use on either the head of the bone on a right side of the patient or a second head of a second bone on a left side of the patient.

Example 13 is an orthopedic system that can optionally include any one or any combination of: a positioning device having a ring portion and a second portion, wherein the second portion can extend outward of the ring portion, and wherein the ring portion can define an aperture configured to seat on a head of a bone; and a guide leg that can define a resection slot configured to guide removal of the head of the bone by resecting a neck of the bone, wherein the guide leg can be configured to couple to the second portion and can be positionally adjustable relative to the second portion and the bone to reference a saddle of the neck of the bone for positioning the guide leg for performing the resection.

Example 14 is the system of Example 13, optionally further comprising: a computer including at least one processor and a memory device, the memory device including instructions that, when executed by the at least one processor, cause the computer to: access image data of a target location including the bone of a patient the image data including at least one of a bone size, a bone orientation and a bone shape; display based upon the collected image data one or more patient-specific characteristics of bone; determine one or more of a size, a shape and an orientation for an osteotomy of the neck of the bone based at least in part upon the one or more patient-specific characteristics of the bone; and convert the one or more patient-specific characteristics of the anatomy of the patient to a setting to position the guide leg relative to the positioning device with reference to the saddle of the neck of the bone.

Example 15 is the system of Example 14, optionally further comprising instructions that cause the computer to construct a virtual model of the bone, wherein the virtual model displays a virtual positioning device and virtual guide leg that approximates the positioning device and the guide leg along with the one or more patient-specific characteristics of the bone of the patient.

Example 16 is the system of any one or any combination of Examples 14-15, wherein the setting can be one of a plurality of standard settings for the guide leg, and the setting can be selected as a best match to the one or more patient-specific characteristics of the bone, and wherein a projection tool and the guide leg can each have indicia corresponding to the plurality of standard setting, including indicia indicative of a distance between the saddle and a center line of the neck of the bone, and wherein the referencing tool can be non-circular in cross-section at a portion that engages the saddle point thereby allowing the referencing tool to be rotated to adjust the guide leg position relative to the neck of the bone.

Example 17 is the system of any one or any combination of Examples 13-16, wherein the second portion can have an outer surface is curved along an extent outward of the ring portion, wherein the outer surface and the curved slot can provide the second portion with a uniform width between the outer surface and the slot, and wherein the guide leg can be configured to couple to the second portion via a first projection that is received in the slot.

Example 18 is the system of any one or any combination of Examples 13-17, wherein the guide leg further optionally defines a slot spaced from the resection slot, and further optionally comprising a referencing tool configured to be received in the slot of the guide leg, wherein the guide leg and referencing tool can be moveable relative to one another via the slot, and wherein the referencing tool can be configured to engage the saddle on the neck of the bone.

Example 19 is the system of Example 18, wherein movement of the guide leg relative to the referencing tool via the slot can adjust a length of resection guided by the resection slot to the neck of the bone.

Example 20 is a method optionally comprising any one or any combination of: coupling a positioning guide to a resection guide; locating a ring portion of the positioning guide on a head of a bone; positioning a referencing tool to rest against a side of the bone distal of the head, wherein positioning the referencing tool adjusts a position of the resection guide relative to the positioning guide and the bone; after positioning, coupling the resection guide to the bone; and resecting the bone at a neck to remove the head, the resection aided by the resection guide.

Example 21 is the method of Example 20, wherein the ring portion of the positioning guide can be positioned on the head of the bone such that a center axis of the ring portion can be aligned with a center axis of head of the bone, and optionally further comprising removing the ring portion prior to resecting the bone.

Example 22 is the method of any one or any combination of Examples 20-21, optionally further comprising: imaging the bone to collect image data regarding at least one of a bone size, a bone orientation and a bone shape of the patient; determining based upon the collected image data one or more patient-specific characteristics of the bone; and converting the one or more patient-specific characteristics of the bone to a setting for the resection guide to position the resection guide relative to the positioning device with reference to the side of the bone distal of the head.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 5B is a perspective view of the referencing tool of FIGS. 5 and 5A.

DETAILED DESCRIPTION

The present application relates an orthopedic assembly and related components, methods and systems for performing a resection to remove a head of a bone at a neck thereof.

Figure 1A:
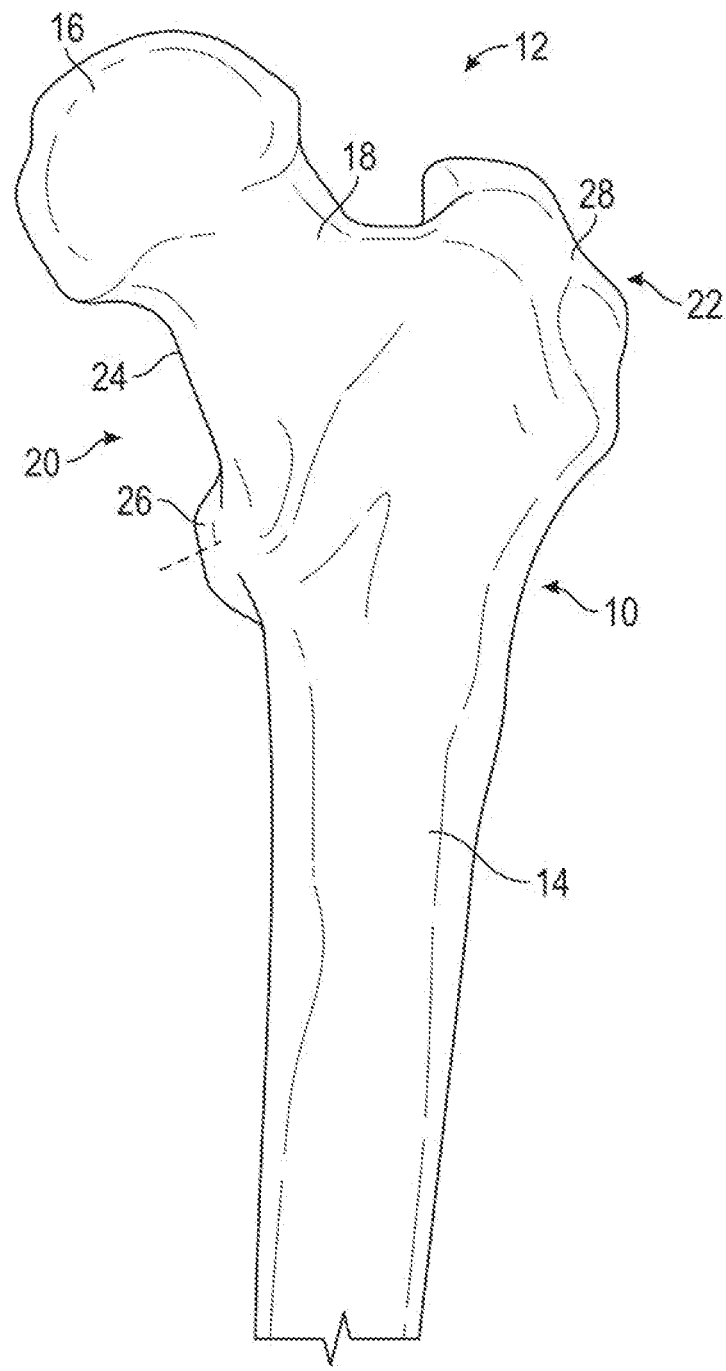
FIG. 1A is a perspective view of a proximal portion of an unresected femur having a femoral head, in accordance with an example of the present disclosure.

FIG. 1A shows a bone 10 comprising a proximal portion 12 of a femur 14. The femur 14 can have a head 16, a neck 18, a medial portion 20 and a lateral portion 22. The medial portion 20 includes a saddle 24 and a lesser trochanter 26. The lateral portion 22 includes a greater trochanter 28.

The head 16 can be the proximal most part of the femur 14 and can be attached to the remainder of the femur 14 by the neck 16. The medial portion 20 can include the lesser trochanter of the femur 14 and surface portions surrounding the lesser trochanter 26 such as the saddle 24 of the neck 18.

Figure 1B:
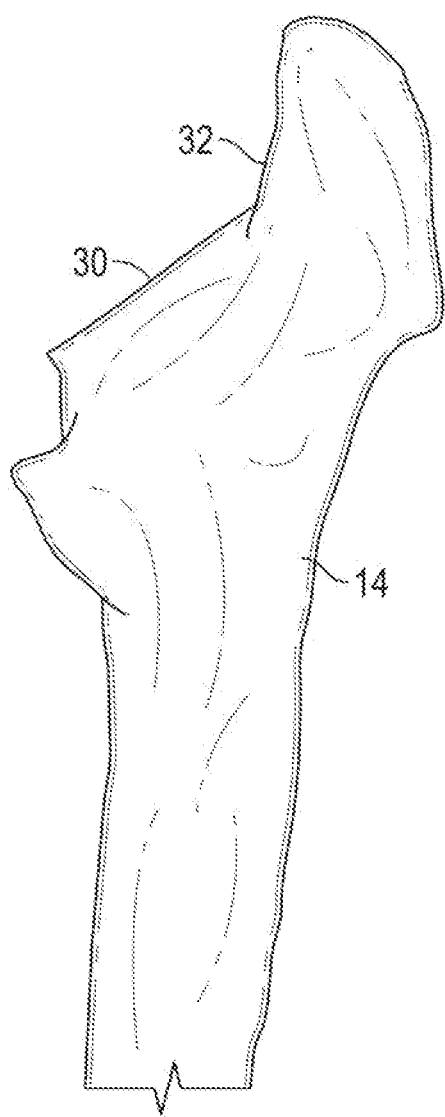
FIG. 1B is a perspective view of the proximal portion of the femur having undergone a neck resection using the devices and techniques disclosed herein to remove a femoral neck and femoral head, in accordance with an example of the present disclosure.

FIG. 1B shows a planar neck resection 30 that has been performed on the femur 14. This neck resection 30 can be guided by the orthopedic assembly as will be described and illustrated subsequently. After guiding the resection 30, the orthopedic assembly can be removed. The surgeon can optionally make by hand (unguided) another resection 32, such as an angled or orthogonal resection to the neck resection 30. Following resection, a broach can be inserted through the neck resection 30 to prepare an intramedullary canal of the femur 14 for receiving a femoral stem of a femoral implant. Various other instruments not specifically shown can be utilized to properly size, select and couple the femoral implant to the femur 14 including femoral stem broaches, broach insertion tools, trunnions, trial femoral heads, etc., which are commercially available from Zimmer Biomet, Warsaw, Ind.

Figure 2:
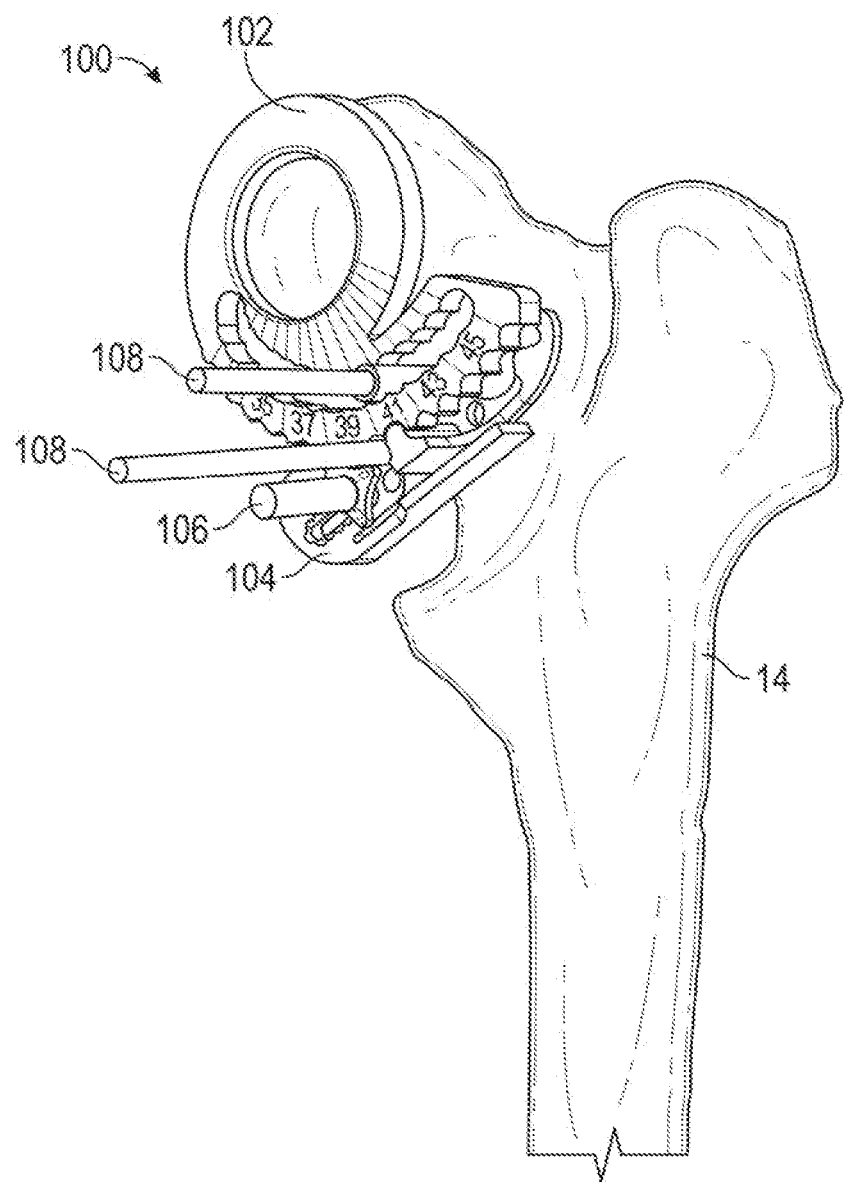
FIG. 2 is a perspective view of an orthopedic assembly secured to the unresected femur of FIG. 1A, the orthopedic assembly including a positioning device and a cut guide, in accordance with an example of the present disclosure.
Figure 2A:
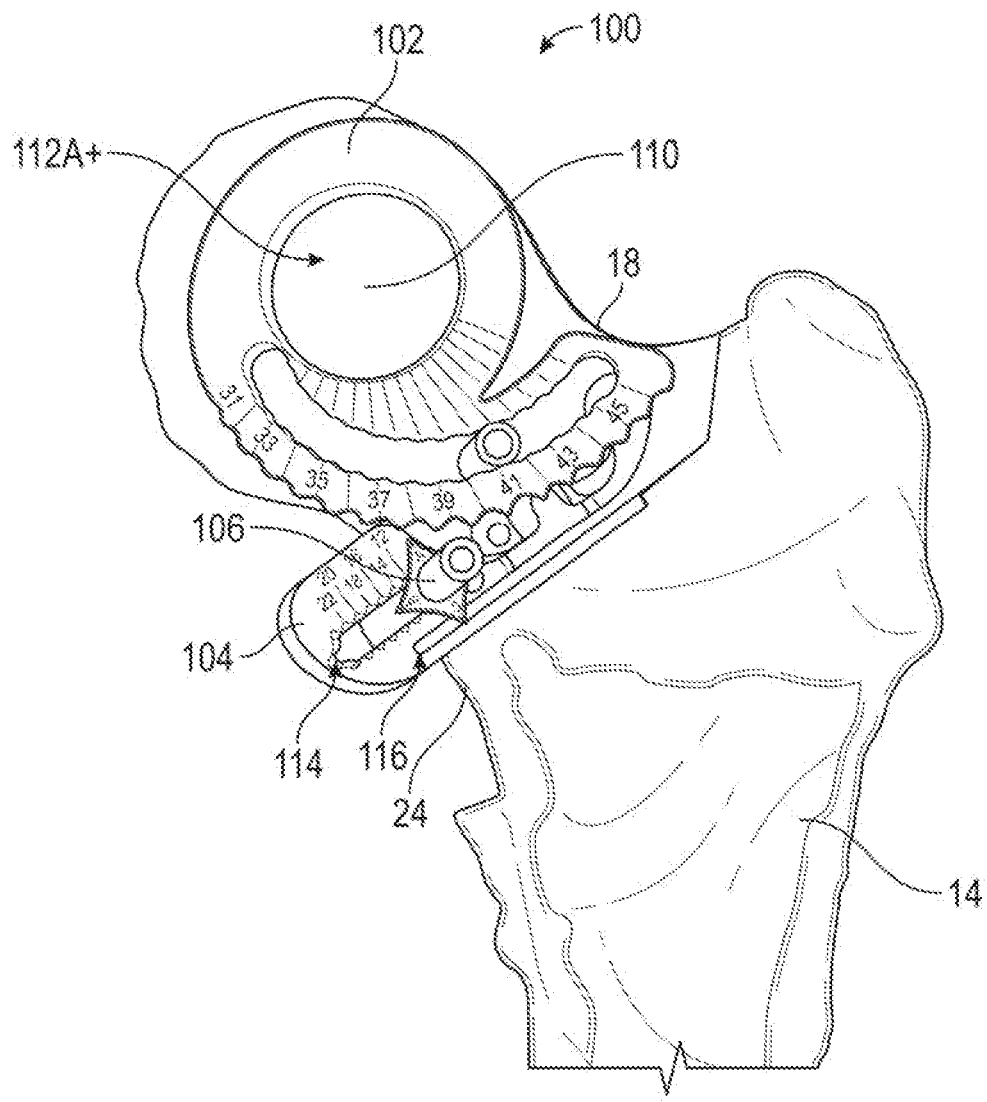
FIG. 2A is a plan view of the orthopedic assembly of FIG. 2 seated on the proximal portion of the femur and also demonstrating a portion of the femoral neck and femoral head the assembly is configured to remove, in accordance with an example of the present disclosure.

FIGS. 2 and 2A show an orthopedic assembly 100 coupled to the femur 14 in a desired position prior to making the neck resection 30 of FIG. 1B. As shown in FIGS. 2 and 2A, the orthopedic assembly 100 can include a positioning device 102, a cut guide 104 (also referred to a guide leg herein) and a referencing tool 106. As shown in FIG. 2, the cut guide 104 can be secured to the femur 14 by one or more pins 108. It should be noted that the positioning device 102 may not be pinned to the femur 14 and can be removed prior to resection.

FIG. 2A shows the orthopedic assembly 100 and the femur 14 in a plan view with proximal portions of the femur 14 that are to be removed with the neck resection 30 (FIG. 1B) aided by the cut guide 104 indicated. As shown in FIG. 2A (and discussed and illustrated subsequently), the positioning device 102 can be configured to size the head 16 of the femur 14 and can be configured to reference a center 110 of the head 16 by seating on the femur 14 with an aperture 112.

The cut guide 104 can be configured to couple with the positioning device 102 in a selectively moveable manner. Thus, the cut guide 104 can be positionally adjustable relative to the positioning device 102 and the femur 14. Alternatively, as further illustrated and discussed the positioning device 102 can be positionally adjustable relative to the cut guide 104 and/or the referencing tool 106. The referencing tool 106 can be configured to couple with the cut guide 104 in a selectively moveable such as by being received in a slot 114 spaced from a resection slot 116 of the cut guide 104. This arrangement allows one or both of the cut guide 104 and the referencing tool 106 to be positionally adjustable relative to one another to adjust a depth and/or orientation of the neck resection 30 (FIG. 1B) guided by the resection slot 116. As shown in FIG. 2A (and discussed and illustrated subsequently), the referencing tool 106 can be configured to engage the saddle 24 to facilitate a desired positioning of the cut guide 104. The positioning device 102, the cut guide 104 and/or the referencing tool 106 can be provided with indicia 118A, 118B, 118BB and 118C (FIG. 3) comprising marks/numbers/letters, respectively. The indicia 118A, 118B can reference a center of the aperture 112

(which can be aligned with the center 110 of the head 16) and can indicate a distance (here in mm) from the center 110 to the neck resection 30 (FIG. 1B). The indicia 118BB and 118C can be used in combination and can indicate a distance from the saddle 24 to a centerline axis of the neck 18. The indicia 118C of the referencing tool 106 can provide indication for incremental adjustment of the cut guide 104 as described subsequently.

Figure 3:
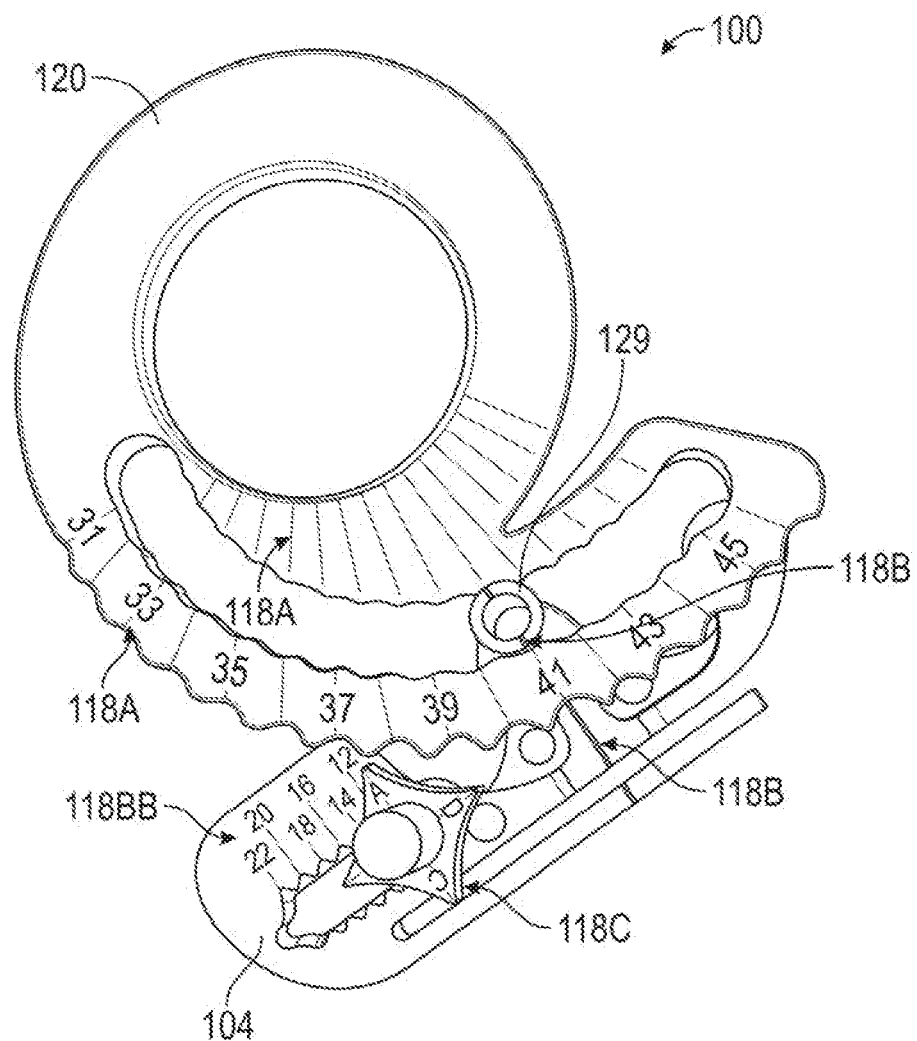
FIG. 3 is a plan view of the orthopedic assembly of FIG. 2, in accordance with an example of the present disclosure.

FIG. 3 shows the orthopedic assembly 100 in isolation with the cut guide 104 coupled to the positioning apparatus 102 via a first projection 129 of the cut guide 104 received in a slot of the positioning apparatus 102. As discussed, the cut guide 104 is moveable within the slot relative to the positioning apparatus 102. Alternatively, the positioning apparatus 102 can be moveable and the cut guide 104 and/or the referencing tool 106 can be positionally fixed. Thus, at least one of the cut guide 104 and the referencing tool 106 is moveable relative to one another to orient the cut guide 104 as desired including by referencing the saddle of the femur, for example.

Figure 3A:
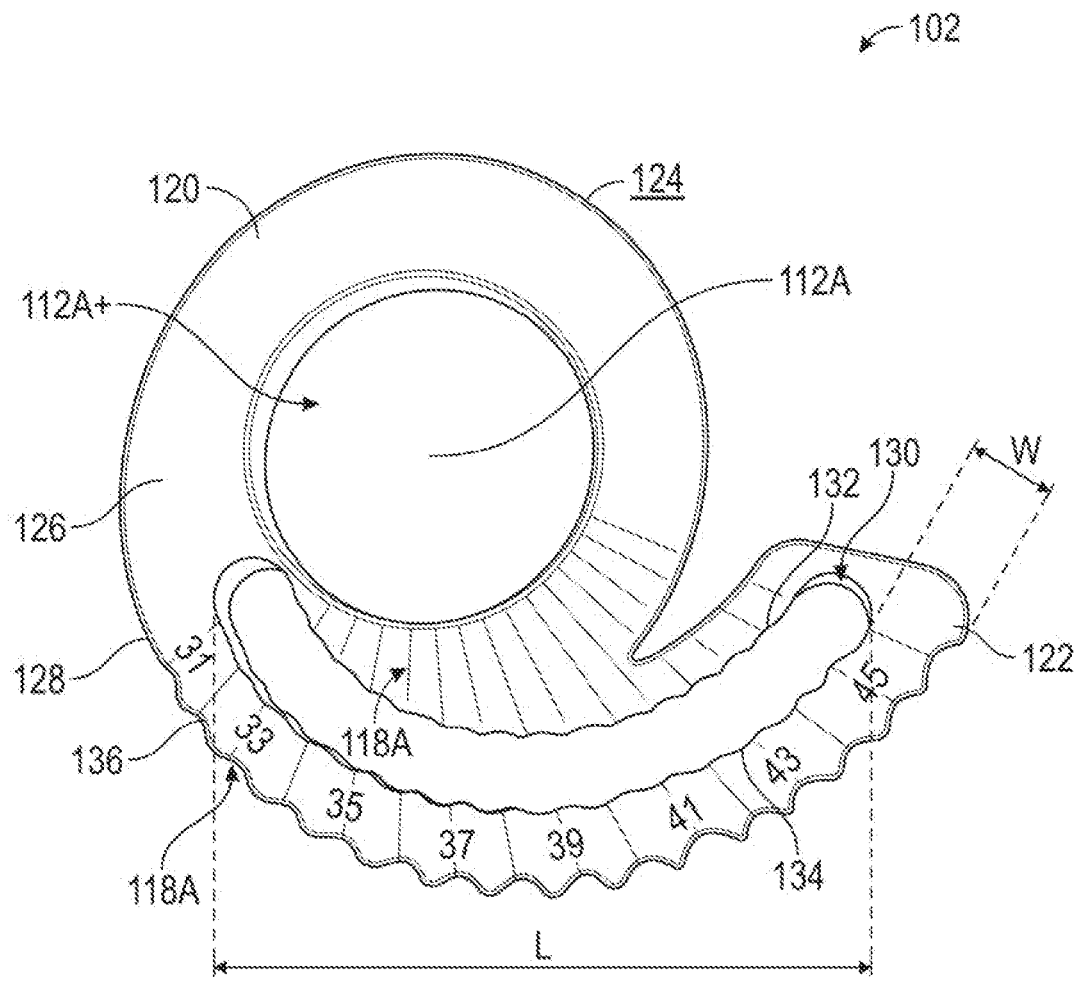
FIG. 3A is a plan view of the positioning device of the orthopedic assembly of FIG. 3 shown in isolation.

FIG. 3A shows the positioning device 102 in isolation. The positioning device 102 can include the indicia 118A, a ring portion 120, a second portion 122, a first side surface 124, a second side surface 126 and an outer surface 128.

Figure 4A:
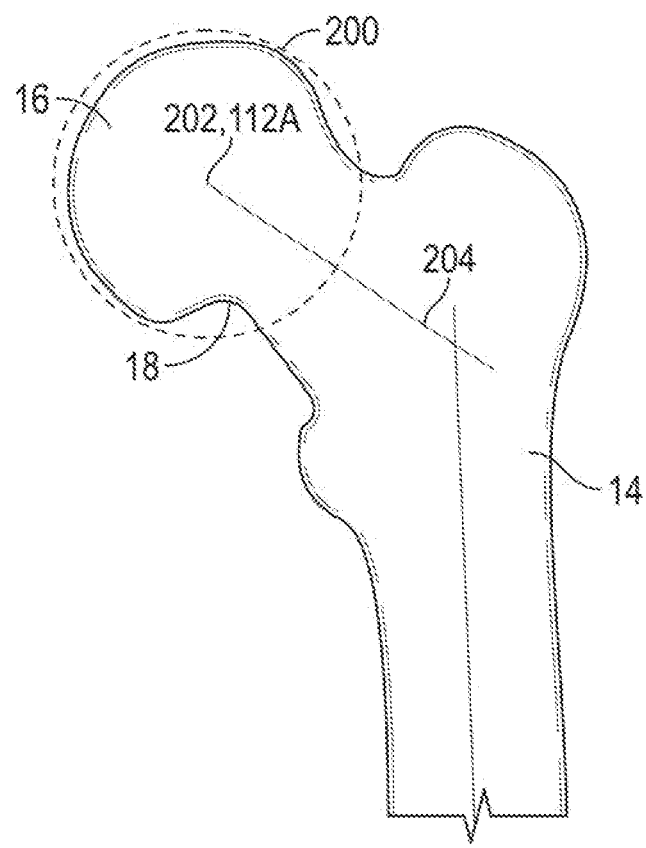
FIGS. 4A and 4B show a methodology whereby the positioning device of FIGS. 3 and 3A is seated on the head of the femur to identify a center of the femoral head, in accordance with an example of the present disclosure.
Figure 4B:
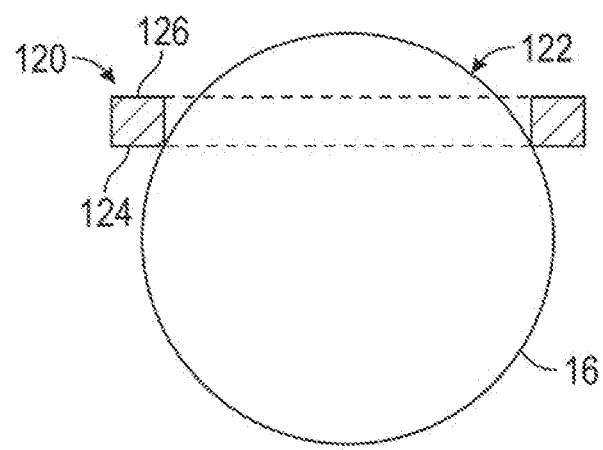

The first side surface 124 can have substantially a same shape as the second side surface 126 such that either surface is configured to seat on the head 16 of the femur 14 in the manner shown in FIG. 2A and FIG. 4B. This configuration allows the orthopedic assembly 100 to be reversable and configured for use on either the head of the femur on a right side of the patient or the head of femur on a left side of the patient.

The ring portion 120 can be configured as a ring having the first side surface 124 and opposing second side surface 126 and defining the aperture 112. The ring portion 120 with the aperture 112 can be configured to seat on the head 16 of the femur 14 (further illustrated in FIG. 4B). As discussed, when the positioning device 102 is seated on the head 16, the center 112A of the aperture 112 can be aligned with the center 110 of the head 16 (reference FIG. 2A). Alternatively, the positioning device 102 can be seated on the head 16, the center 112A of the aperture 112 may not be aligned with the center 110. Rather, the positioning device 102 can just be contacted in a stable manner (e.g., at two or more locations with the head 16).

The second portion 122 can be connected to the ring portion 120. The second portion 122 can comprise a curved or spiral shaped arm that extends outward of the ring portion 120 with a curved extent including along the outer surface 128. The second portion 122 can define a slot 130 that is curved along a first length L. The slot 130 can extend substantially almost an entirety of a length of the second portion 122 and can extend into the ring portion 120. In some examples, the slot 130 could communicate with the aperture 112. In some examples, only a portion of the length L of the slot 130 may be curved.

As shown in the example of FIG. 3A, the second portion 122 can be configured to define a first plurality of detents 132 arranged along a first side of the slot 130 for at least a portion of the first length L and defines a second plurality of detents 134 arranged along a second side of the slot 130 for at least a portion of the first length L. The second plurality of detents 134 can oppose and can be generally aligned with the first plurality of detents 132 across a width of the slot 130. The first plurality of detents 132 and the second plurality of detents 134 can be configured for coupling the cut guide 104 to the positioning device 102 in a desired incremental manner as shown in FIG. 3 via the first projection 129 of the cut guide 104.

The outer surface 128 along the second portion 122 can have a curved extent outward of the ring portion 120. The second portion 122 can be shaped with the outer surface 128 and the slot 130 such that the second portion 122 has a uniform width W between the outer surface 128 and the slot 130 along the length L (or at least a portion of the length L). Thus, the positioning device 102 can be configured to have a consistent width from the centers of two circles (circles in the slot 130 to circle on surface 128). The second portion 122 can be configured to define a third plurality of detents 136 arranged along the outer surface 128 of the second portion 122. The third plurality of detents 136 can generally align with the first plurality of detents 132 and/or the second plurality of detents 134 but can be spaced therefrom by at least the width W of the second portion 122.

The ring portion 120 and/or the second portion 122 can include the indicia 118A extending along a portion of one or both thereof. The indicia 118A can include lines, for example and/or numbers. As discussed previously, the indicia 118A reference a distance from the center 112A of the aperture 112, a distance from the center 110 of the femur 14 to the head resection 30 (FIG. 1B), and/or other desired criteria. According to some examples, the orthopedic assembly 100 or various components thereof such as the positioning device 102, cut guide 104, etc. may not utilize indicia or have indicia that differ from those illustrated in the FIGURES. Thus, indicia as described herein can be optional.

Figure 3B:
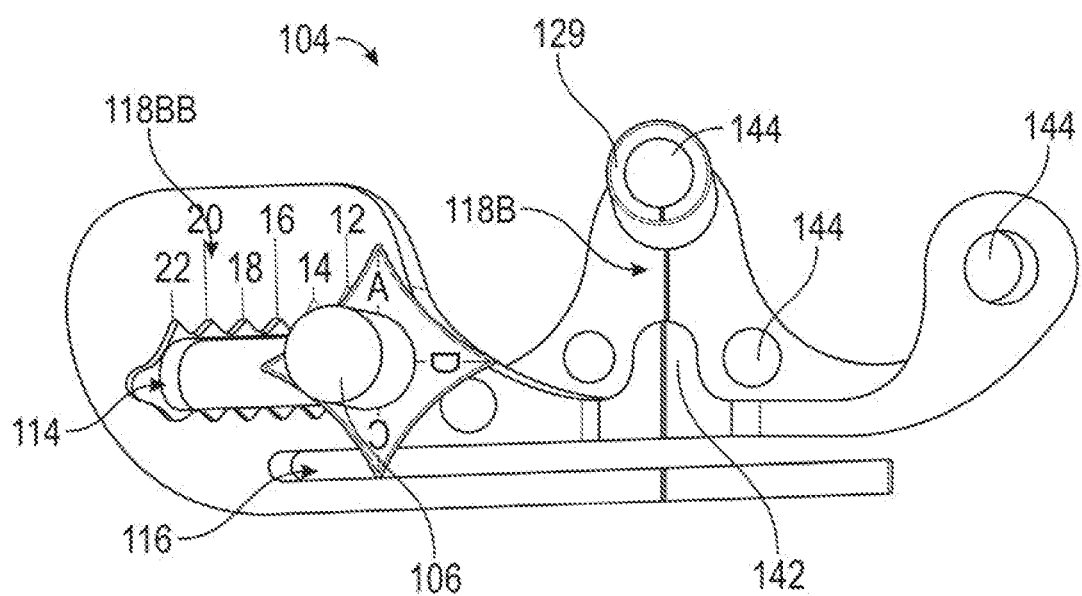
FIG. 3B is a plan view of the cut guide and referencing tool of the orthopedic assembly of FIG. 3 shown in isolation.

FIG. 3B shows the cut guide 104 and the referencing tool 106. The referencing guide 106 can be captured by the cut guide 104 and can have a longitudinal length that extends a generally orthogonal direction to a longitudinal length of the cut guide 104. The cut guide 104 is configured as a guide leg of the orthopedic assembly 100. The cut guide 104 can include the slot 114, the resection slot 116, the indicia 118B, 118BB, the first projection 129, a second projection 142 and one or more holes 144.

The cut guide 104 can define the slot 114 and the resection slot 116, which can be spaced from one another and can be generally aligned to as to extend in substantially a parallel manner. As discussed previously, the resection slot 116 can be configured to guide an instrument such as a saw in removal of the head 16. The slot 114 can be configured to receive the referencing tool 106.

As is previously illustrated in FIGS. 2, 2A and 3, the cut guide 104 can be configured to couple to the second portion 122 via the first projection 129 that is received in the slot 130 and is held by the first plurality of detents 132 and the second plurality of detents 134, for example. A shown in the example of FIG. 3B, the second projection 142 is spaced from the first projection 129 a distance corresponding to the width W of the second portion 122 (reference FIG. 3A). The second projection 142 and the first projection 129 can be spaced apart such that the first projection 129 is received in the slot 130 and the second projection 142 engages the outer surface 128 of the second portion 122. The second projection 142 can extend substantially parallel with the first projection 129. The first projection 129 and the second projection 142 can be configured to engage with the first plurality of detents 132, the second plurality of detents 134 and the third plurality of detents 136, respectively. In this manner the cut guide 104 can couple with the positioning device 102 (FIG. 3A).

The one or more holes 144 can be spaced along a longitudinal length of the cut guide 104 at various longitudinally and/or latitudinal spaced locations. The one or more holes 144 can comprise pin holes configured to receive pins 108 as illustrated in FIG. 2 to secure the cut guide 104 to the bone. According to the example of FIG. 3B, the first projection 129 can be cannulated to define one of the one or more holes 144.

The indicia 118B can include one or more lines configured to be aligned with the lines of the positioning device 102, for example. These lines can be on the first and second projections 129, 142 and other portions of the cut guide 104. The indicia 118BB can comprise numbers and/or lines. As discussed previously, the indicia 118BB can be configured reference a distance from the saddle of the neck to a centerline axis of the neck of the femur, a depth of resection of the cut guide, and/or other desired criteria.

FIGS. 4A and 4B are a highly schematic views of one methodology that can be implemented by the orthopedic assembly 100 with reference to the femur 14. This methodology (and that of FIG. 6B) can be implemented electronically using a computer with the systems and methods as further described herein including in reference to FIG. 7. FIG. 4A shows a dashed circle 200 corresponding generally to the ring portion 120 of the positioning device 102 as previously discussed. The dashed circle 200 has a center 202 corresponding to the center 112A of the aperture 112. The circle 200 can be positioned relative to the head 16 such that the center 202 thereof is aligned with the center 110 of the head 16 of the femur 14. Alternatively, the center 202 of the circle 200 may not be aligned with the center 110 but just contacted in a stable manner (e.g., at two or more locations) with the head 16. The centerline 204 of the neck 18 of the femur 14 can then be calculated as intersecting and extending from the center 110. FIG. 4B shows the ring portion 120 having the first side surface 124, the second side surface 126 and the aperture 112 and positioned to seat on the head 16 (illustrated in a highly schematic manner) of the femur 14 via the aperture 112, which is configured to receive a portion of the head 16.

Figure 5:
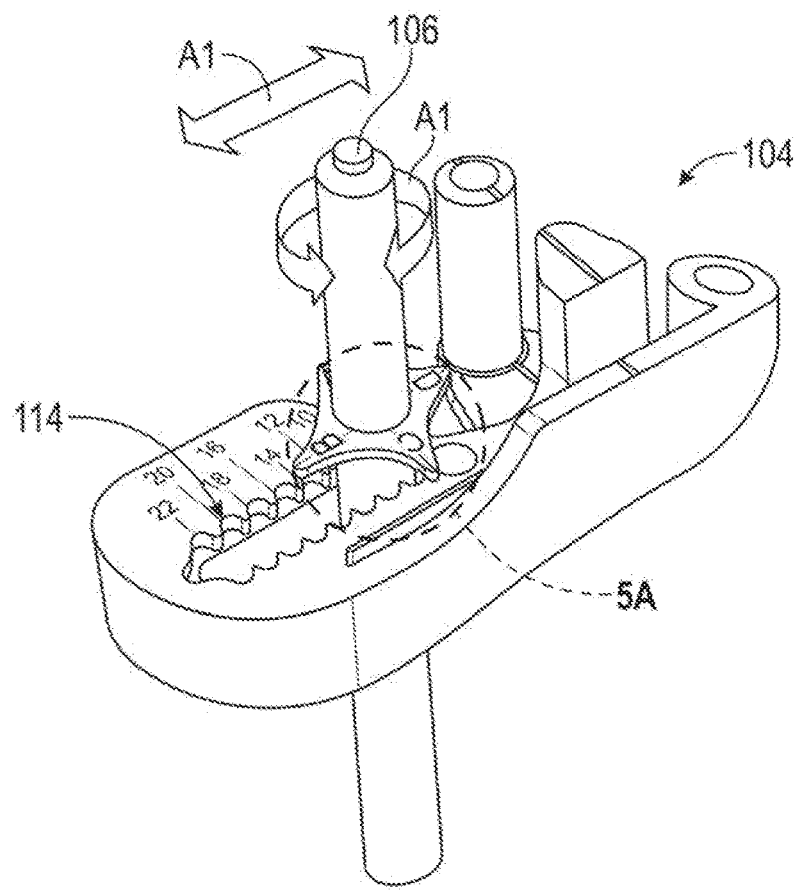
FIG. 5 is a perspective view of the cut guide and referencing tool of FIGS. 3 and 3B illustrating movement of the referencing tool relative to the cut guide, in accordance with an example of the present disclosure.

FIG. 5 illustrates the referencing tool 106 and the cut guide 104 can be positionally adjustable (i.e. moveable as indicated by arrow A1) relative to one another utilizing the slot 114. The referencing tool 106 can be configured to be received in the slot 114 of the cut guide 104. As discussed previously, movement of the cut guide 104 relative to the referencing tool 106 via the slot 114 adjusts a length of the neck resection 30 (FIG. 1B) guided by the resection slot 116 to the neck 18 (FIG. 1A). Alternatively, as previously discussed, in other examples the positioning apparatus 102 can be moveable (e.g., rotatable about the center of the humeral head) and the cut guide 104 and/or the referencing tool 106 can be positionally fixed.

Figure 5A:
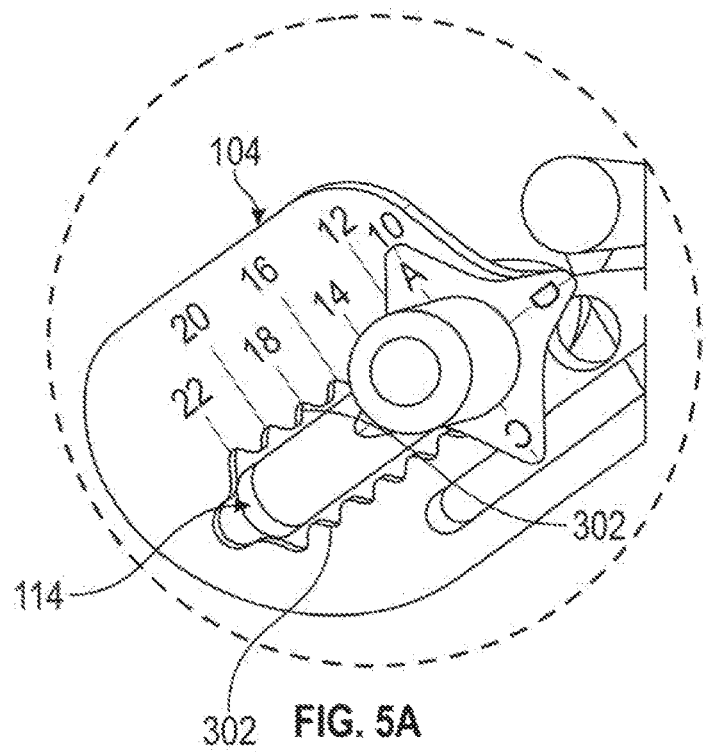
FIG. 5A is an enlarged view of a positioning slot of the cut guide receiving the referencing tool of FIG. 5.

As shown in FIG. 5A, the cut guide 104 can include detents 302 arranged along either side of the slot 114. These can selectively lock the referencing tool 106 and cut guide together 104. The detents 302 can correspond in position with one or more of the indicia 118BB. The detents 302 can be configured to interact with flute projections 304 of the referencing tool 106 to facilitate coupling of the cut guide 104 and referencing tool 106. The flute projections 304 are shown in FIG. 5B and are disposed adjacent projections 306 that carry the indicia 118C. As shown in FIG. 5B, the referencing tool 106 can be configured as a shaft having a longitudinal axis L and a proximal end shaped as a handle 308 to project from the cut guide 104 when received in the slot 114 (reference FIG. 5). The referencing tool 106 can have a distal portion 310 that is non-circular (e.g., oval, truncated oval, egg-shaped, elliptical, etc. in cross-section orthogonal to the longitudinal axis L. Put another way, the distal portion 310 is non-cylindrically shaped as shown in FIG. 5B.

Figure 6A:
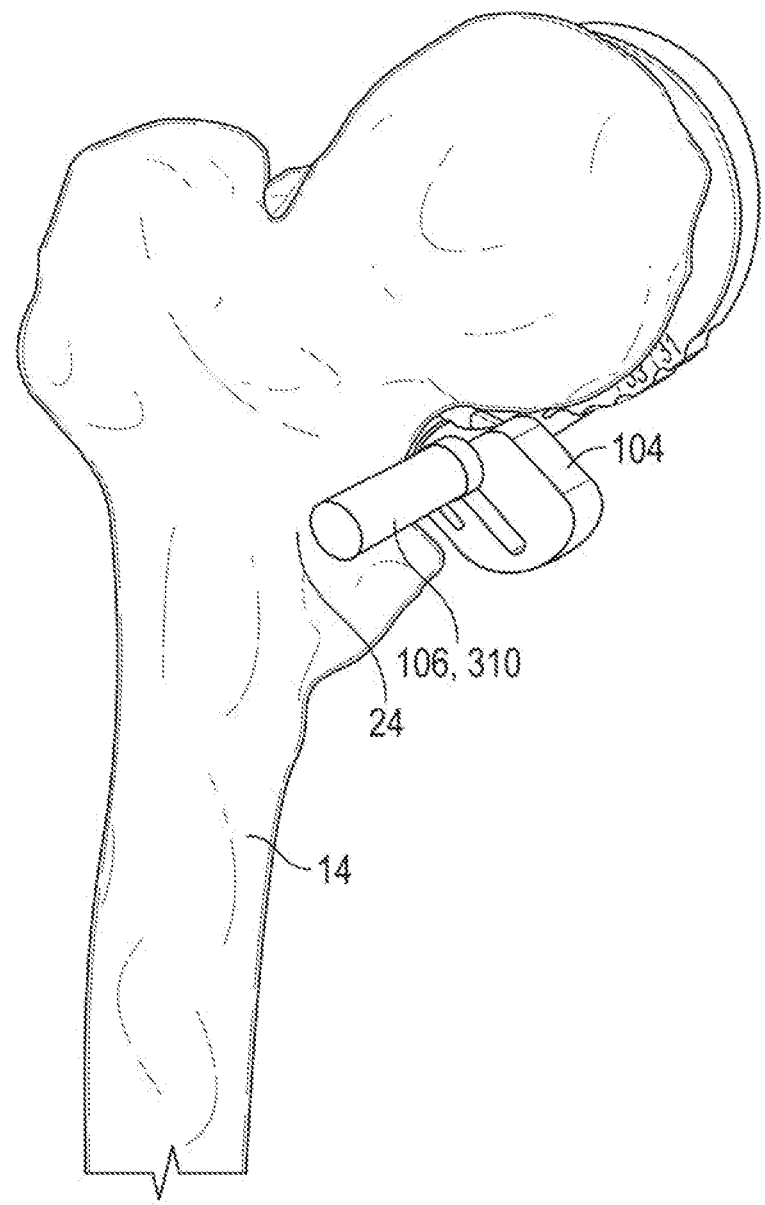
FIG. 6A is a perspective view of the referencing tool positioned to engage a saddle of a neck of the femur, in accordance with an example of the present disclosure.

Returning to FIG. 5, the referencing tool 106 can be configured to allow for movement of the cut guide 104 relative thereto (and relative to the femur) in an incremental manner (e.g., 0.5 mm resolution of movement of the cut guide 104 along arrow A1 per a quarter turn of the referencing tool 106). More particularly, the referencing tool 106 can be moved/raised proximally to disengage the flute projections 304 from the detents 302, the referencing tool 106 can then be rotated as shown by arrow R. This rotation brings different parts of a circumference of the distal portion 310 into contact the saddle 24 of the femur 14 as shown in FIG. 6A. The distal portion 310 can be shaped in a manner such that a quarter turn of the referencing tool 106 to align a different one of the flute projections with a same detent as was previously engaged can provide for a desired movement (e.g., 0.125 mm 0.25 mm, 0.5 mm, etc.) of the cut guide 104 along the arrow A1.

FIG. 6A shows the referencing tool 106, in particular, the distal portion 310 thereof projecting from the cut guide 104 and engaging the saddle 24 of the femur 14. According to some examples, the cut guide 104 can be positioned as desired relative to the referencing tool 106 and femur 14 with referencing tool 106 remaining in engagement with the saddle 24.

Figure 6B:
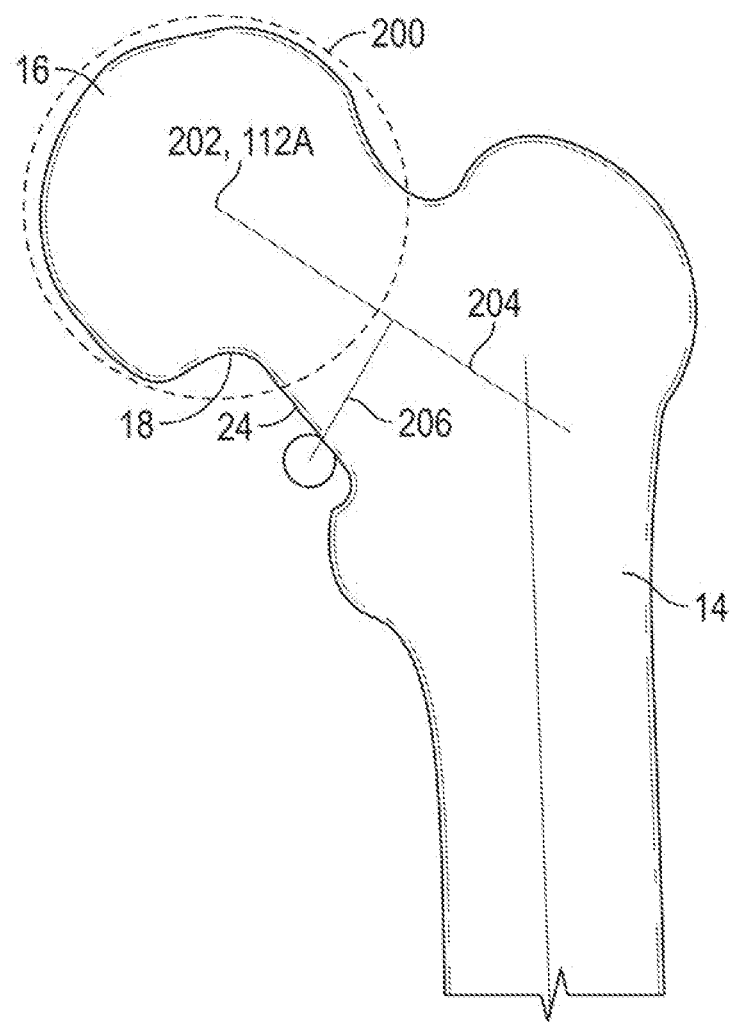
FIG. 6B is a methodology whereby the orthopedic assembly is used to reference a centerline axis of the neck of the femur and a distance from the saddle of the neck of the femur to the centerline axis of the neck of the femur using the positioning device, the referencing tool and the cut guide in combination, in accordance with an example of the present disclosure.

FIG. 6B is a further highly schematic view the methodology of FIGS. 4A and 4B that can be implemented by the orthopedic assembly 100 with reference to the femur 14. FIG. 6B, as with FIG. 4A, shows the dashed circle 200 corresponding generally to the ring portion 120 of the positioning device 102 as previously discussed. The dashed circle 200 has the center 202 corresponding to the center 112A of the aperture 112. The circle 200 can be positioned relative to the head 16 such that the center 202 thereof is aligned with the center 110 of the head 16 of the femur 14. Alternatively, the circle 200 may not need to be aligned with the center 110 but just contacted in a stable manner (e.g., at two or more locations) with the head 16. The centerline 204 of the neck 18 of the femur 14 can then be calculated as intersecting and extending from the center 110. FIG. 6B further demonstrates a point of engagement with the saddle 24 can be used to generate a line 206 that intersects with the centerline 204 of the neck 18 in the manner (same orientation and/or position) of the resection slot 116 of the cut guide 104. Thus, according to some examples, the line 206 can correspond generally with the neck resection 30 of FIG. 1B. The angle of the intersection between the line 206 and the centerline 204 can be orthogonal or another angle depending upon the desired version for neck resection. A distance of the line 206 can also be measured and can correspond to the indicia 118BB and 118C of the cut guide 104 and the referencing tool 106. For example, if the distance of the line 206 to the intersection from the saddle is determined to be 10 mm, the referencing tool 106 and cut guide 104 can be set to a setting of 10 A. In another example, if the distance of the line 206 to the intersection to the saddle 24 is determined to be 10.25 mm, the referencing tool 106 and cut guide 104 can be set to a second setting of 10 B.

Figure 6C:
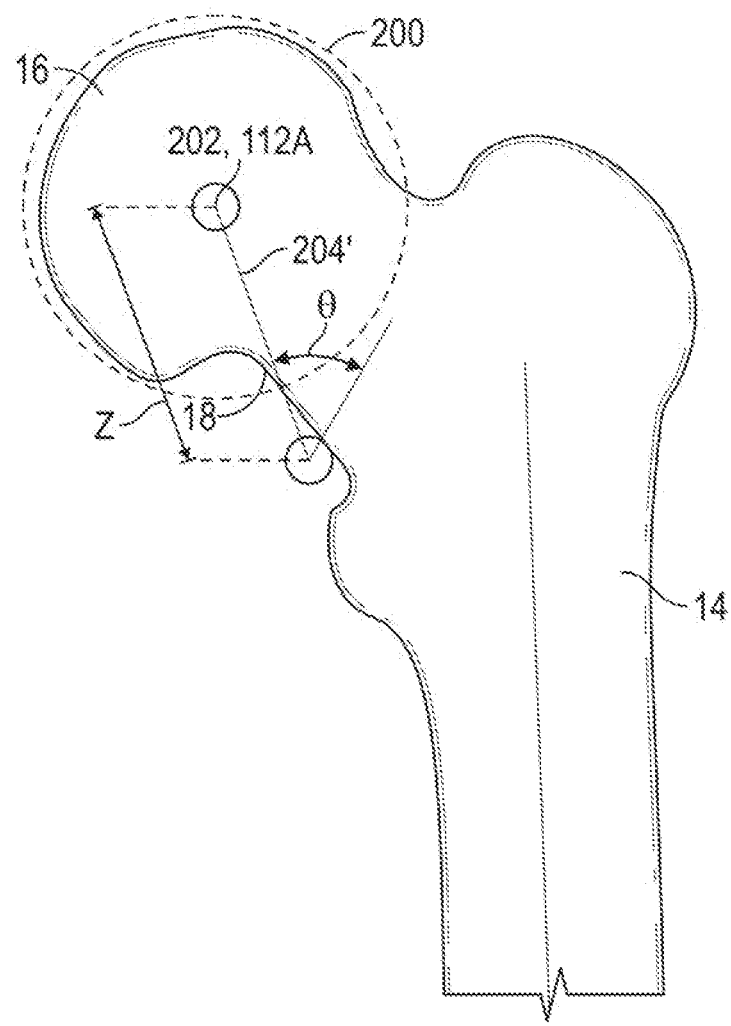
FIG. 6C is another methodology using the orthopedic assembly using the positioning device and the referencing tool in combination, in accordance with an example of the present disclosure.

FIG. 6C shows a further highly schematic view of an alternative methodology that can be implemented by the orthopedic assembly 100 with reference to the femur 14. FIG. 6C methodology shows an example where the positioning apparatus 102 can be moveable (e.g., relative to the humeral head) and the cut guide 104 and/or the referencing tool 106 can be positionally fixed. In FIG. 6C, as with FIGS.

4A and 6B, shows the dashed circle 200 corresponding generally to the ring portion 120 of the positioning device 102 as previously discussed. The dashed circle 200 has the center 202 corresponding to the center 112A of the aperture 112. The circle 200 can be positioned moveable relative to the head 16 such that the center 202 thereof is aligned with the center of the head 16 of the femur 14. Alternatively, the circle 200 may not need to be aligned with the center 110 but just contacted in a stable manner (at two or more locations) with the head 16. A line 204' having a distance Z and offset at an angle θ from a centerline of the neck 18 can then be calculated as intersecting and extending from the center 112A of the aperture 112 to the locating tool 106, which is maintained in contact with the saddle of the femur 14 while the positioning device 102 is moved.

In some examples, the orthopedic assembly such as the one previously described can be used as part of systems and methods of generating and outputting data comprising position settings for purposes of tailoring the orthopedic assembly such that the cut guide can be used to create a patient appropriate femoral neck resection having a desired location, length, and/or orientation. It should be noted, however, that the virtual surgery planning systems and methods discussed herein are optional and the orthopedic assembly can be used without them.

The orthopedic assembly disclosed herein can be aided by the use of computer-assisted image methods based on two-dimensional or three-dimensional images of the patient's bones and/or adjacent anatomy generated by magnetic resonance imaging ("MRI"), computer tomography ("CT"), ultrasound, X-ray, or other medical imaging techniques. Various computer aided drafting ("CAD") programs and/or other software can be utilized for the image reconstruction of the anatomy (in three-dimensions or two-dimensions) from the medical scans of the patient, such as, for example, commercially available software.

Various pre-operative planning procedures and related patient-specific instruments are disclosed in commonly assigned and pending or now issued U.S. patent application Ser. No. 11/756,057, filed May 31, 2007; U.S. patent application Ser. No. 11/971,390, filed on Jan. 9, 2008; U.S. patent application Ser. No. 12/025,414, filed on Feb. 4, 2008; U.S. patent application Ser. No. 12/039,849 filed on Feb. 29, 2008; U.S. patent application Ser. No. 12/103,824, filed Apr. 16, 2008; U.S. patent application Ser. No. 12/371,096, filed Feb. 13, 2009; U.S. patent application Ser. No. 12/483,807, filed Jun. 12, 2009; U.S. patent application Ser. No. 12/872,663, filed Aug. 31, 2010; U.S. patent application Ser. No. 12/973,214, filed Dec. 20, 2010; and U.S. patent application Ser. No. 12/978,069, filed Dec. 23, 2010. The disclosures of the above applications are incorporated herein by reference.

The systems and methods can draw upon preoperative surgical plans. These plans can be formulated for a specific patient. A preoperative surgical plan can encompass virtual surgery planning with the aid of a computer, as will be discussed subsequently. The systems and method can allow for interactive input from the patient's physician or other medical professional according to some examples. Imaging data from medical scans of the relevant anatomy of the patient can be obtained at a medical facility or doctor's office, using any of the medical imaging techniques discussed previously. The imaging data can include, for example, various medical scans of a relevant bone (here the femur 14), bones or other relevant portion of the patient's anatomy, as needed for virtual anatomy modeling and, optionally, for virtual determination of resection size, shape (e.g. angle) and relative orientation. The imaging data, thus obtained, and other associated information can be used to construct a computer (digital) image of the anatomy of the patient. The preoperative surgical plan can further include the identification and selection of particular bone portions that need to be removed or retained, virtual orientation of the orthopedic device as disclosed herein on the femur, virtual implantation of an orthopedic implant, etc. Such selections such as the length orientation of the resection can be made to best match the patient's anatomical need. For example, the disclosed orthopedic assembly including the cut guide can be configured to have various settings to adjust the position of the cut guide, length of the cut guide, etc. Such settings can be standard settings that are not necessarily patient-specific, but can be adjusted based on data output to the physician comprising various size settings that most closely match the needs of the patient based upon the patient's anatomy. These size settings can be visually displayed to the physician as part of the surgical plan. Thus, referring back to the example of FIG. 6B, the centerline 204 and line 206 can be virtually determined and the distance of the line 206 to the intersection with the centerline 204 determined. If the distance of the line 206 to the intersection from the saddle 24 is determined to be 10 mm, the virtual surgery planning aid would display a setting of 10 A indicating the referencing tool 106 and cut guide 104 should be set to the setting of 10 A.

The virtual model of the patient's anatomy can be viewed on a computer display or other electronic screen and can also be reproduced as a hard copy on disk or other medium and viewed by direct or indirect or backlight illumination. The model can be sized for viewing on any appropriate screen size and may be cropped, rotated, etc., as selected by the individual (e.g., the physician) viewing the screen. The three-dimensional model can illustrate diseased bone that should be removed and can identify the shape and orientation of the resection(s) to be used in removal of the diseased bone, etc. The three-dimensional model can further illustrate the orthopedic assembly overlaid on the bone such as in FIG. 2B and can show the relevant cuts according to one example.

As previously discussed, the orthopedic device 100 can be fabricated with various standard markings or indicia indicative of various lengths, such as A, B, C, for indicia 118C. A marking "A" of the orthopedic device 100 can correspond to a virtual output "A" displayed to the user. Put another way, the orthopedic device 100 can be set to a most appropriate length (such as "A") as indicated or suggested by the system output.

According to one example, a method is disclosed that optionally utilizes imaging data from a patient and performs calculations from the imaging data including determining locations of bone geometry and structure. From the calculations, surgical decisions including the positioning of instruments such as the orthopedic assembly 100 can be determined. The surgical decisions can be visualized electronically prior to being implemented. Based upon the visualization, the physician can alter his or her decision as desired.

Figure 7:
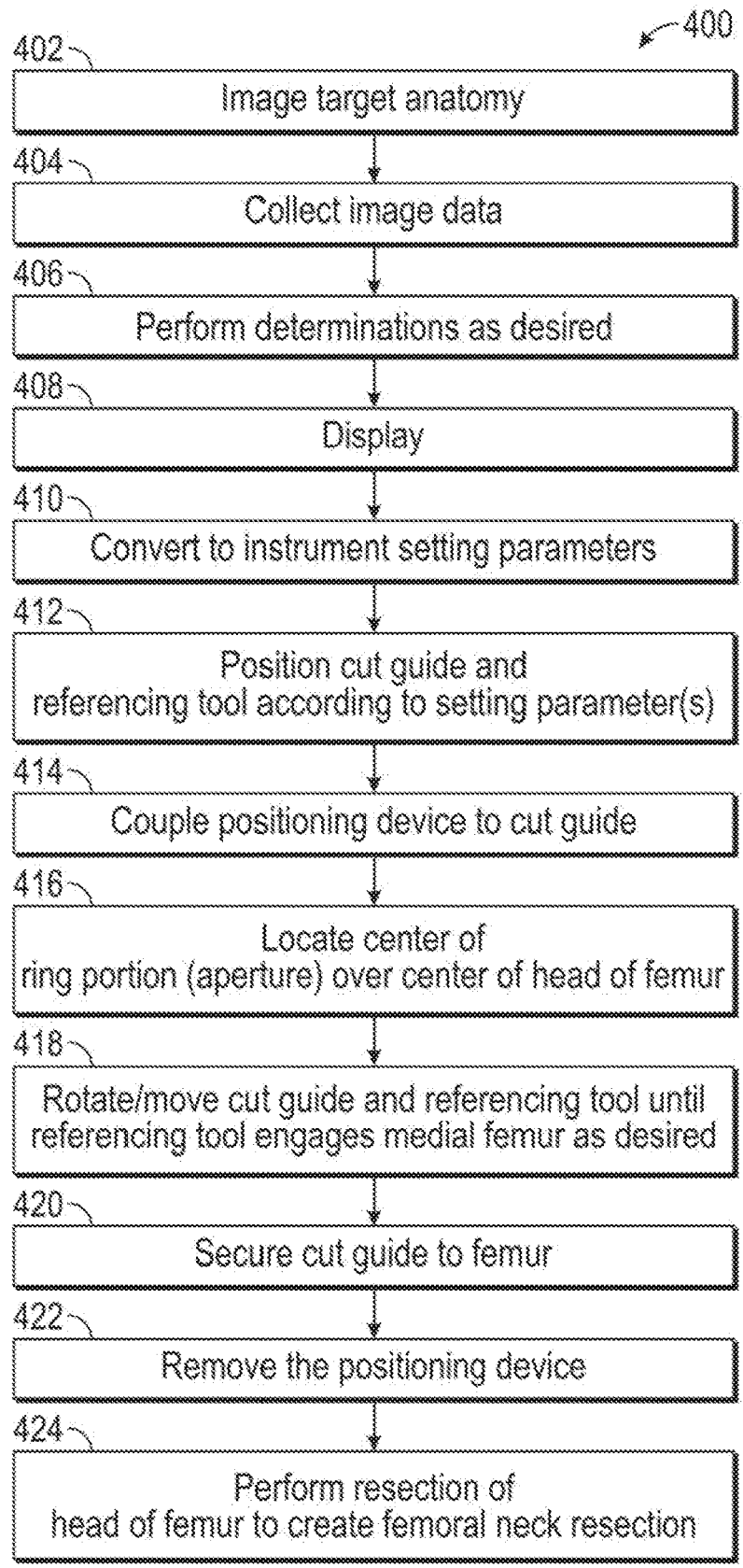
FIG. 7 is a flowchart illustrating a method of resecting a proximal portion of a bone including using virtual surgery planning, in accordance with an example of the present disclosure.

FIG. 7 shows a flow chart of a method 400 according to one example of the present application. The method 400 can include aspect for virtual surgery planning and implementation using the orthopedic assembly 100, for example. However, as noted above the virtual surgical planning aspects of the method 300 are optional and may not be utilized in many cases.

At a high level, the example of FIG. 7 can include: imaging a target location of an anatomy of a patient (here a proximal femur) to collect image data regarding at least one of a bone size, a bone orientation and a bone shape of the patient; displaying based upon the collected image data, one or more patient-specific characteristics of the anatomy of the patient; determining one or more of a size, a shape and an orientation for at least one bone resection based at least in part upon the one or more patient-specific characteristics of the anatomy of the patient; and outputting information about the patient-specific characteristics to allow for selection of appropriate settings for the orthopedic assembly 100.

As is further illustrated in the example of FIG. 7, imaging 402 can be performed of the patient's anatomy of interest (a target location) using any one or combination of the technology previously discussed. Such scanning can collect 404 image data of the patient's anatomy of interest. Such image data can include at least one of a bone size, a bone orientation and a bone shape of the patient, for example. The collected image data can be stored such as in a database, file or other known medium including the Cloud. Image processing of the image data can be performed as desired (e.g., to sharpen or contrast the image, to better identify anatomical surface features, etc.). The method 400 can perform 406 calculations to describe and/or characterized the geometry of bone in the anatomy of interest. The calculations can be performed upon the stored image data corresponding to the target location. These calculations can determine or describe, for example, patient-specific characteristics such as bone dimensions, bone axes/landmarks/positions, relative positions between bone portions, curvature and surface topography of the bone surface, and/or soft tissue attachment size and/or location, and the like. According to further examples, the calculations can be used to determine and/or describe the geometry and other characteristics of diseased bone that may require removal. According to some examples, the calculations can be used to determine and/or describe the geometry and other characteristics of bone that may not be removed during the procedure and can determine the patient-specific characteristics (e.g., bone dimensions, bone axes/landmarks/positions, relative positions between bone portions, curvature and surface topography of the bone surface, etc.) of that bone, in addition to or in alternative to the diseased bone.

The method 400 can determine 406 an appropriately-sized, shaped and/or oriented one or more resections to remove the diseased bone. Such determination can consider patient-specific characteristics regarding both the diseased bone and/or any adjacent bone that may be retained. The method can display 410 data to a physician or other personnel. For example, the display 410 can include a patient-appropriate setting(s) (e.g., what location along the slot 130 to insert and couple the first projection 129 in, what location along the slot 114 to insert and couple the referencing tool 106 in, etc.) for the orthopedic assembly 100 as previously illustrated as described. According to another example, the display step 410 can include displaying data about the anatomy of interest and/or data regarding the area of interest to a physician or other personnel. Such displaying can further include display of patient-specific characteristics (e.g., diseased and/or healthy bone dimensions, bone orientation, surface topography, or the like). In some examples, displaying can include virtual assembly and/or arrangement of the orthopedic assembly 100 of the anatomy of interest, for example. The displaying can further include display of patient-specific characteristics (dimensions, orientation, etc.) of the one or more resections, or other aspects of the femur, which can be based at least in part upon the one or more patient-specific characteristics of the anatomy of the patient.

Method 300 can further convert 412 various of the patient-specific characteristics (e.g., size, shape, orientation, etc.) of the virtual bone grafts to corresponding setting parameters (e.g. relative length(s), shape, orientation of various cut slots, etc.) for the orthopedic device 100. According to some examples, the corresponding setting parameters can be displayed so that the appropriate setting can be made to the orthopedic assembly 100.

FIG. 7 also shows implementation of the method 400 to perform resection. This can be done with or without the virtual surgical planning of steps 402-412 as discussed previously. At step 414, the cut guide and referencing tool can be positioned relative to one another and/or the positioning device and cut guide can be coupled together. This can be done based upon physician measurement of the femur including a measurement to determine the centerline axis of the neck of the femur. Alternatively, the setting can be done according to the setting parameters provided by the virtual surgical planning tool. The method 400 can locate 416 a center of the ring portion (i.e. the aperture) over the center of the head of the femur as previously illustrated and described. At step 418, the cut guide can be positionally adjusted by rotating the referencing tool and moving the cut guide until the referencing tool engages the medial femur (saddle) as desired. Step 418 may not be necessary in some examples where virtual surgical planning has been utilized or can be performed at physician discretion.

At step 420 the cut guide can be secured to the femur such as by pinning the cut guide thereto. After pinning, the positioning device can be removed at step 422. The method 400 can perform resection of the head of the femur to create the neck resection previously described and illustrated in reference to FIG. 1B.

Figure 8A:
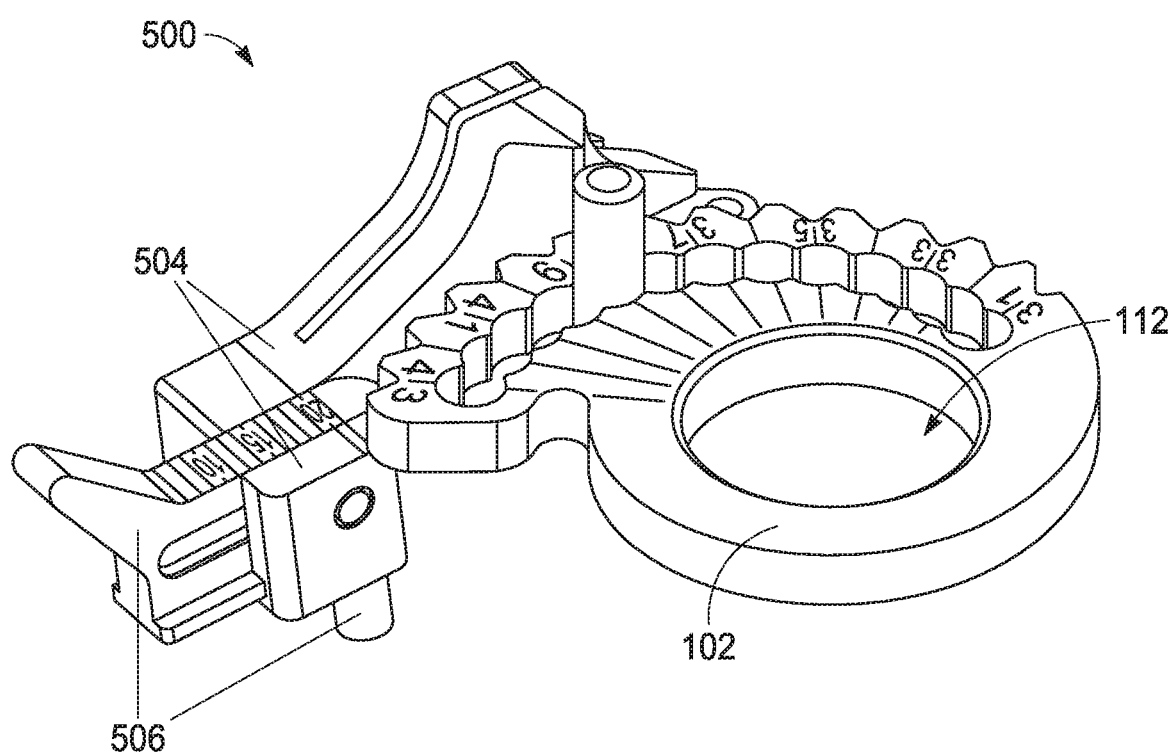
FIG. 8A is a perspective view of a cut guide and referencing tool according to another example of the present disclosure.
Figure 8B:
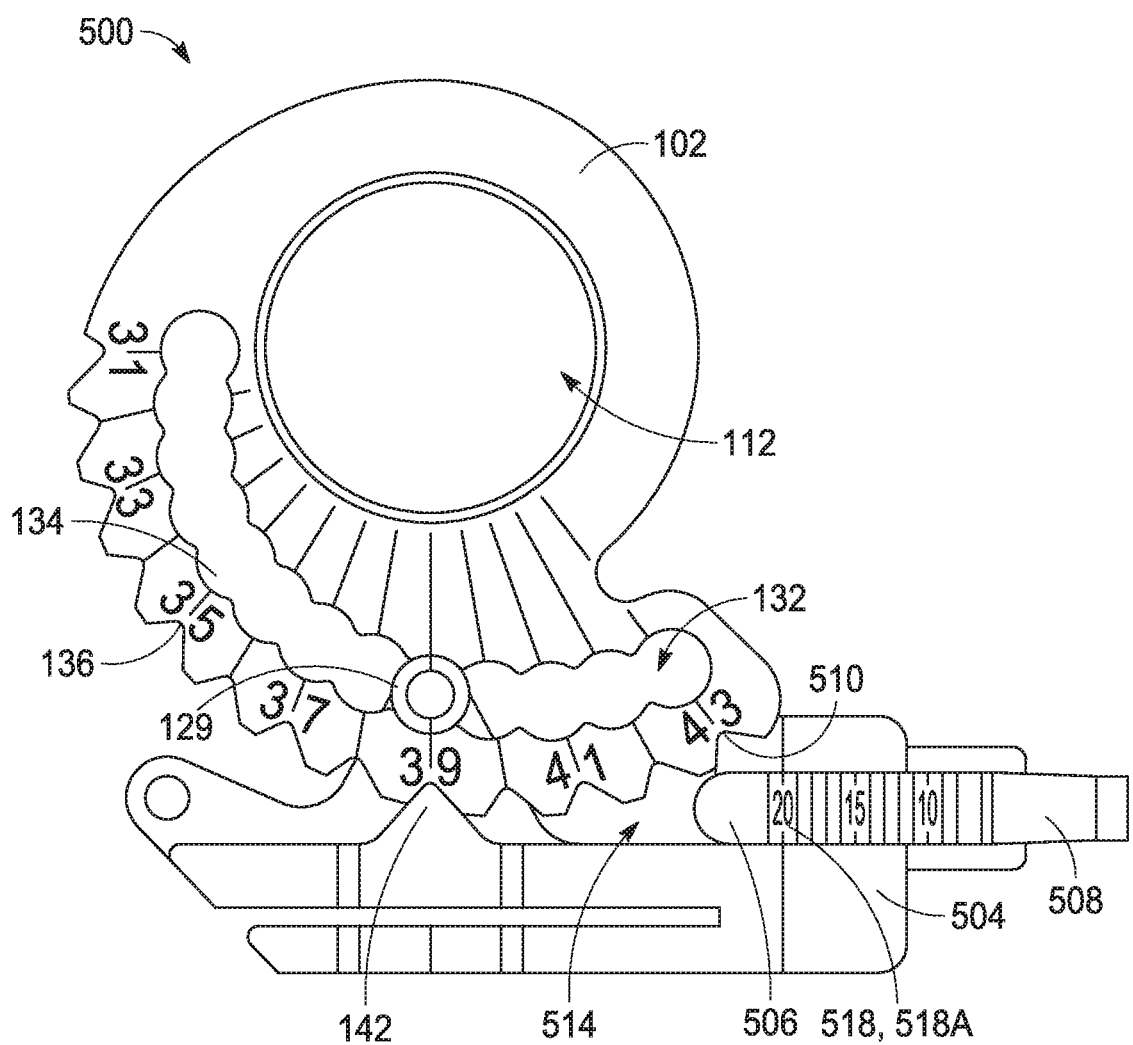
FIG. 8B is a perspective view of the orthopedic assembly of FIG. 8A.

FIGS. 8A and 8B show another example of an orthopedic assembly 500 that is similar to the orthopedic assembly 100 of FIGS. 2-6B. Similar to the orthopedic assembly 100, the orthopedic assembly 500 can include the positioning device 102, a cut guide 504 (also referred to a guide leg herein) and a referencing tool 506.

The orthopedic assembly 500 can be operated in the manner of the orthopedic assembly 100 discussed previously to perform the neck resection 30 (FIG. 1B) aided by the cut guide 504. As discussed previously, the positioning device 102 can be configured to size the head 16 of the femur 14 and can be configured to reference a center 110 of the head 16 by seating on the femur 14 with an aperture 112.

The cut guide 504 can be configured in a similar manner to the cut guide 104 unless otherwise indicated. Similarly, the referencing tool 506 can be configured in the manner as the referencing tool 106 unless otherwise indicated. The cut guide 504 can be configured to couple with the positioning device 102 in a selectively moveable manner. Thus, the cut guide 504 can be positionally adjustable relative to the positioning device 502 and the femur 14 (FIG. 1). The positioning device 102 can be positionally adjustable relative to the cut guide 504 and/or the referencing tool 506. The referencing tool 506 can be configured to couple with the cut guide 504 in a selectively moveable manner.

Referencing now FIG. 8B, the orthopedic assembly 500 differs from that of orthopedic assembly 100 in that slot 514 has been altered in shape from the slot 114 of the orthopedic assembly 100. The referencing tool 506 now can include a sizer portion 518 with indicia 518A in addition to the shaft. This sizer portion 518 can be configured to be received in and can be moveable relative to the slot 514 and can reference indicia on the cut guide 504. To facilitate movement, the referencing tool 506 can include a first tab 508 configured to be engaged by a finger or thumb of a physician.

The cut guide 504 can additionally include a second tab 510 comprising a projection 512 configured to engage one of the third plurality of detents 136 of the positioning device 102. The second tab 510, in addition to the first projection 129 and the second projection 142 can be configured to engage with the first plurality of detents 132, the second plurality of detents 134 and the third plurality of detents 136. In this manner the cut guide 104 can couple with the positioning device 102.

As shown in FIGS. 8A and 8B, the referencing tool 506 can be configured to engage the saddle 24 of the femur to facilitate a desired positioning of the cut guide 504. The positioning device 102, the cut guide 504 and/or the referencing tool 506 can be provided with indicia (including indicia 518A) comprising marks/numbers/letters, respectively. The indicia can be used as previously discussed to reference a center of the aperture 112 (which can be aligned with the center 110 of the head 16) and can indicate a distance (here in mm) from the center 110 to the neck resection 30 (FIG. 1B). The indicia including 518A can be used in combination and can indicate a distance from the saddle 24 to a centerline axis of the neck 18. The indicia 518A of the referencing tool 506 can provide indication for incremental adjustment of the cut guide 504 as previously described.

Additional Notes

Certain examples are described herein as including logic or a number of components, modules, or mechanisms. Modules may constitute either software modules (e.g., code embodied on a machine-readable medium or in a transmission signal) or modules. A module is tangible unit capable of performing certain operations and may be configured or arranged in a certain manner. In examples, one or more computer systems (e.g., a standalone, client or server computer system) or one or more modules of a computer system (e.g., a processor or a group of processors) may be configured by software (e.g., an application or application portion) as a module that operates to perform certain operations as described herein.

In various examples, a module may be implemented mechanically or electronically. For example, a module may comprise dedicated circuitry or logic that is permanently configured (e.g., as a special-purpose processor, such as a field programmable gate array (FPGA) or an application-specific integrated circuit (ASIC)) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in dedicated and permanently configured circuitry, or in temporarily configured circuitry (e.g., configured by software) may be driven by cost and time considerations.

Accordingly, the term "module" can be understood to encompass a tangible entity, such as hardware, that can be that an entity that is physically constructed, permanently configured (e.g., hardwired) or temporarily configured (e.g., programmed) to operate in a certain manner and/or to perform certain operations described herein. Considering examples in which modules are temporarily configured (e.g., programmed), each of the modules need not be configured or instantiated at any one instance in time. For example, where the modules comprise a general-purpose processor configured using software, the general-purpose processor may be configured as respective different modules at different times. Software may accordingly configure a processor, for example, to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In examples in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some examples, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example examples, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Examples may be implemented in digital electronic circuitry, or in computer hardware, firmware, software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of examples may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures require consideration. Specifically, it will be appreciated that the choice of whether to implement certain functionality in permanently configured hardware e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various examples.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "of" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An orthopedic system comprising:
   a positioning device having a ring portion and a second portion, wherein the second portion extends outward of the ring portion, wherein the ring portion defines an aperture configured to seat on a head of a bone, and wherein the positioning device defines a curved slot; and
   a guide leg defining a slot and further defining a resection slot configured to guide removal of the head of the bone by resecting a neck of the bone, wherein the guide leg is configured to couple to the second portion and is positionally adjustable relative to the second portion and the bone via the curved slot of the positioning device;
   a referencing tool configured to engage and thereby reference a saddle of the neck of the bone, wherein the referencing tool is received in the slot of the guide leg, and wherein the guide leg is moveable relative to the referencing tool via the slot to adjust a length of resection guided by the resection slot to the neck of the bone.

2. The system of claim 1, further comprising:
   a computer including at least one processor and a memory device, the memory device including instructions that, when executed by the at least one processor, cause the computer to:

access image data of a target location including the bone of a patient, the image data including at least one of a bone size, a bone orientation and a bone shape;

display based upon the image data one or more patient-specific characteristics of bone;

determine one or more of a size, a shape and an orientation for an osteotomy of the neck of the bone based at least in part upon the one or more patient-specific characteristics of the bone; and convert the one or more patient-specific characteristics of the bone of the patient to a setting to position the guide leg relative to the positioning device with reference to the saddle of the neck of the bone.

3. The system of claim 2, further comprising instructions that cause the computer to construct a virtual model of the bone, wherein the virtual model displays a virtual positioning device and virtual guide leg that approximates the positioning device and the guide leg along with the one or more patient-specific characteristics of the bone of the patient.

4. The system of claim 2, wherein the setting is one of a plurality of standard settings for the guide leg, and the setting is selected as a best match to the one or more patient-specific characteristics of the bone, and wherein the positioning device and the guide leg each have indicia corresponding to the plurality of standard setting, including indicia indicative of a distance between the saddle and a center line of the neck of the bone, and wherein the referencing tool is non-circular in cross-section at a portion that is configured to engage the saddle thereby allowing the referencing tool to be rotated to adjust the position of the guide leg relative to the neck of the bone.

5. The system of claim 1, wherein the second portion has an outer surface is curved along an extent outward of the ring portion, wherein the outer surface and the curved slot are curved to provide the second portion with a uniform width between the outer surface and the curved slot, and wherein the guide leg is configured to couple to the second portion via a first projection that is received in the curved slot.

6. An orthopedic system comprising:

a positioning device having a ring portion and a second portion, wherein the ring portion defines an aperture configured to allow the ring portion to seat on a head of a bone, and wherein the second portion extends from the ring portion, wherein the second portion defines a slot that is curved along a first length;

indicia along a portion of one or both of the ring portion and the second portion; and a guide leg defining a second slot and further defining a resection slot configured to guide removal of the head of the bone by resecting a neck of the bone, wherein the guide leg is configured to couple to the second portion and is positionally adjustable relative to the second portion and the bone via the slot of the positioning element;

a referencing tool configured project from the guide leg to engage and thereby reference a saddle of the neck of the bone, wherein the referencing tool is received in the slot of the guide leg, and wherein the guide leg is moveable relative to the referencing tool via the second slot to adjust a length of resection guided by the resection slot to the neck of the bone.

7. The system of claim 6, wherein the second portion defines a first plurality of detents arranged along a first side of the slot for at least a portion of the first length and defines a second plurality of detents arranged along a second side of the slot for at least the portion of the first length, wherein the second plurality of detents oppose and are generally aligned with the first plurality of detents across a width of the slot.

8. The system of claim 7, wherein the second portion has an outer surface that is curved along an extent outward of the ring portion, and wherein the outer surface and the slot provide the second portion with a uniform width between the outer surface and the slot for the first length.

9. The system of claim 8, wherein the second portion defines a third plurality of detents arranged along at least a portion of the outer surface of the second portion, wherein the third plurality of detents generally align with the first plurality of detents.

10. The system of claim 6, wherein the guide leg is configured to couple to the second portion via a first projection that is received in the slot of the second portion.

11. The system of claim 10, wherein the guide leg defines a plurality of pin holes therein, and wherein the first projection is cannulated defining one pin hole of the plurality of pin holes.

12. The system of claim 10, wherein the guide leg has second projection extending substantially parallel with the first projection, and wherein the second projection and the first projection are spaced apart such that the first projection is received in the slot and the second projection engages an outer surface of the second portion.

13. The system of claim 10, wherein the guide leg defines the second slot spaced from the resection slot, and the referencing tool is configured to be received in the second slot of the guide leg, and wherein the guide leg and referencing tool are moveable relative to one another via the second slot.

14. The system of claim 6, wherein the referencing tool and the guide leg each have indicia, including indicia indicative of a distance between the saddle and a center line of the neck of the bone, and wherein the referencing tool is non-circular in cross-section at a portion that engages the saddle thereby allowing the referencing tool to be rotated to adjust the guide leg position relative to the neck of the bone.

15. The system of claim 6, wherein the ring portion and the second portion have a first side and a second side, and wherein the first side has a substantially similar shape as the second side such that the positioning device is reversable and configured for use on either the head of the bone on a right side of a patient or a second head of a second bone on a left side of the patient.

* * * * *

UNITED STATES PATENT AND TRADEMARK OFFICE
CERTIFICATE OF CORRECTION

PATENT NO. : 11,642,137 B2
APPLICATION NO. : 17/079019
DATED : May 9, 2023
INVENTOR(S) : Mulqueen et al.

Page 1 of 1

It is certified that error appears in the above-identified patent and that said Letters Patent is hereby corrected as shown below:

In the Claims

In Column 19, Line 57, in Claim 6, after "configured", insert --to--

Signed and Sealed this
Twenty-seventh Day of June, 2023

Katherine Kelly Vidal
*Director of the United States Patent and Trademark Office*